US008903481B2

(12) United States Patent
Kelly et al.

(10) Patent No.: US 8,903,481 B2
(45) Date of Patent: Dec. 2, 2014

(54) SYSTEM FOR CONTEXTUAL DISPLAY OF DATA FROM AN IMPLANTABLE MEDICAL DEVICE

(75) Inventors: Jonathan H. Kelly, Woodbury, MN (US); James Kalgren, Lino Lakes, MN (US); Durga Kulkarni, Minneapolis, MN (US); Daniel Patrick Holmdahl, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 601 days.

(21) Appl. No.: 12/273,861

(22) Filed: Nov. 19, 2008

(65) Prior Publication Data

US 2009/0156909 A1 Jun. 18, 2009

Related U.S. Application Data

(60) Provisional application No. 61/013,751, filed on Dec. 14, 2007.

(51) Int. Cl.
*A61B 5/044* (2006.01)
*A61B 5/00* (2006.01)

(52) U.S. Cl.
CPC ............ *A61B 5/0031* (2013.01); *A61B 5/7435* (2013.01); *A61B 5/743* (2013.01); *A61B 5/0006* (2013.01); *A61B 5/044* (2013.01)
USPC ....................................... 600/523

(58) Field of Classification Search
CPC ...... A61B 5/0006; A61B 5/044; A61B 5/742; A61B 5/743; A61B 5/7435; A61B 5/7445
USPC ............... 607/30, 59; 600/523–525
See application file for complete search history.

(56) References Cited

U.S. PATENT DOCUMENTS

| 4,562,841 | A | | 1/1986 | Brockway et al. |
| 5,487,755 | A | * | 1/1996 | Snell et al. ................ 607/27 |
| 5,549,654 | A | * | 8/1996 | Powell ................ 607/32 |
| 5,697,959 | A | * | 12/1997 | Poore ................ 607/32 |
| 6,038,476 | A | * | 3/2000 | Schwartz ................ 607/27 |
| 6,237,398 | B1 | | 5/2001 | Porat et al. |
| 6,675,044 | B2 | * | 1/2004 | Chen ................ 607/30 |
| 6,937,900 | B1 | | 8/2005 | Pianca et al. |

(Continued)

OTHER PUBLICATIONS

"Guidant System Guide for Ventak Prizm, Ventak Prizm He and Ventak Prizm 2", *Guidant Corporation* 2008, pp. 1-331.

(Continued)

*Primary Examiner* — Carl H Layno
*Assistant Examiner* — Eugene Wu
(74) *Attorney, Agent, or Firm* — Pauly, DeVries Smith & Deffner, LLC.

(57) ABSTRACT

Embodiments of the invention are related to data management systems, amongst other things. In an embodiment, the invention includes a video output and a processor in communication with the video output, wherein the video output and the processor are configured to display information regarding a patient in a first format and a second format through the video output simultaneously, the first format comprising a graphical formal and the second format comprising a textual format, the information displayed in the first format divided into a plurality of phases, wherein the system is configured to automatically change the information displayed in the second format based on user selection of one of the plurality of phases. Other embodiments are also included herein.

10 Claims, 9 Drawing Sheets

(56) References Cited

U.S. PATENT DOCUMENTS

| | | |
|---|---|---|
| 6,978,182 B2 | 12/2005 | Mazar et al. |
| 7,041,468 B2 | 5/2006 | Drucker et al. |
| 2005/0197823 A1* | 9/2005 | Werner et al. .................. 703/22 |
| 2007/0270675 A1 | 11/2007 | Kane et al. |

OTHER PUBLICATIONS

"Guidant System Guide for Vitality 2", *Guidant Corporation* 2008, pp. 1-305.

* cited by examiner

SYSTEM FOR CONTEXTUAL DISPLAY OF DATA FROM AN IMPLANTABLE MEDICAL DEVICE

This application claims the benefit of U.S. Provisional Application No. 61/013,751, filed Dec. 14, 2007, the content of which is herein incorporated by reference.

TECHNICAL FIELD

This disclosure relates generally to medical systems and, more particularly, to medical systems that display information from implanted medical devices, amongst other things.

BACKGROUND OF THE INVENTION

Many types of implantable medical devices gather and record data regarding the physiological state of the patient in which they are implanted and details of applied therapy. By way of example, an implantable cardiac rhythm management (CRM) device may gather and record data regarding heart rhythm, information regarding hemodynamics, details regarding electrical stimulation pulses that have been administered, and the like.

Clinicians may periodically access and review data gathered by implantable medical devices. By way of example, when a patient comes in for an appointment an external device, such as a programmer/recorder/monitor (PRM) device, may be used to access information stored by the implantable device. This information may then be stored and/or viewed by a clinician in order to assess the health of the patient and support treatment decisions.

However, the sheer amount of data provided by the implantable device may make effective use of the data challenging. In general, the more information that is presented simultaneously the more complex the display of the information becomes, resulting in a less user-friendly system.

For at least these reasons, a need exists for systems and methods of effectively displaying data gathered by an implantable medical device.

SUMMARY OF THE INVENTION

Embodiments of the invention are related to medical systems that display information from implanted medical devices, amongst other things. In an embodiment, the invention includes a medical system including a video output and a processor in communication with video output. The system can be configured to display information regarding a patient in a first format and a second format through the video output simultaneously. The first format can be a graphical format, such as a graph of data over time, and the second format can be a textual format. The information displayed in the graphical format can be divided into a plurality of phases and the information displayed in the textual format can relate to one of the phases. The system can be configured to automatically change the information displayed in the textual format based on user selection of one of the plurality of phases.

In an embodiment, the invention includes a medical system including an implanted medical device and an external medical system including a telemetry circuit, a video output, and a processor. The telemetry circuit can be configured to receive information regarding a patient from the implanted medical device. The system can be configured to display data regarding the patient divided into a plurality of phases and simultaneously display overview data regarding a particular user-selected phase. The system can be configured to automatically change the overview data as the particular user-selected phase changes.

In an embodiment, the invention includes a device including a graphical display and a machine-readable medium comprising instructions. The instructions can perform various operations when implemented by one or more processors. By way of example, the operations can include communicating with an implantable medical device, providing an image on the graphical display, including providing a representative image of data gathered from the implantable medical device over time divided into multiple phases, receiving a user selection of a particular phase, and providing information on the graphical display regarding the particular phase selected by the user.

In an embodiment, the invention includes a method of operating a medical device. The method can include communicating with an implantable medical device, providing an image on a graphical display, including providing a representative image of data gathered by the implantable medical device over time divided into multiple phases, receiving a user selection of a particular phase, and providing information on the graphical display regarding the particular phase selected by the user.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

An implantable medical device can generate a substantial amount of data regarding the patient in which it is implanted. Frequently, this data is provided to a clinician or system user through a video output device, such as a display screen. However, the display of too much data may introduce undesired complexity. Specifically, when too much data is displayed, it may be difficult for a user to quickly identify and focus on the most important data.

Addressing this issue, embodiments of the invention can include systems and methods for efficiently presenting data from an implantable medical device on a display screen. In accordance with various embodiments herein, data can be displayed in a contextually appropriate manner, simplifying the display of the data and allowing a user to focus on the data that is of greatest interest.

In an embodiment, a medical system is provided including a video output channel and a processor in communication with video output channel. The medical system can be configured to display information regarding a patient in a first format and a second format through the video output channel simultaneously. The first format can be a graphical format, such as a graph of data over time. The second format can be a textual format, such as a tabular display of correlated data. The information in the first graphical format can be data gathered from the patient, such as electrogram data. The information displayed in the first graphical format can be divided into a plurality of phases.

In some embodiments, the data in the first format can represent primary data, while the data in the second format can represent secondary data. Primary data can represent data taken directly from a sensor. Examples of primary data can include electrogram data, pressure data, chemical concentration data, temperature data, and the like. Secondary data can represent data that is related to primary data, but which is different than primary data in that it represents a summary of primary data (such as an average, high, or low of primary data), highlights of primary data, or information that is otherwise related to a particular phase of primary data.

The system can be configured to allow a user to select one or more of the plurality of phases. The information displayed in the second textual format can relate to the selected phase(s). The information displayed in the second textual format can represent data that is correlated to or related to the selected phase. For example the correlated data can represent highlight, summary, and/or aggregate data regarding the selected phase or phases. In this manner, the information displayed in the second textual format can represent a subset of relevant data that is appropriately displayed as the user selects phases of data displayed in the first graphical format.

Figure 1:
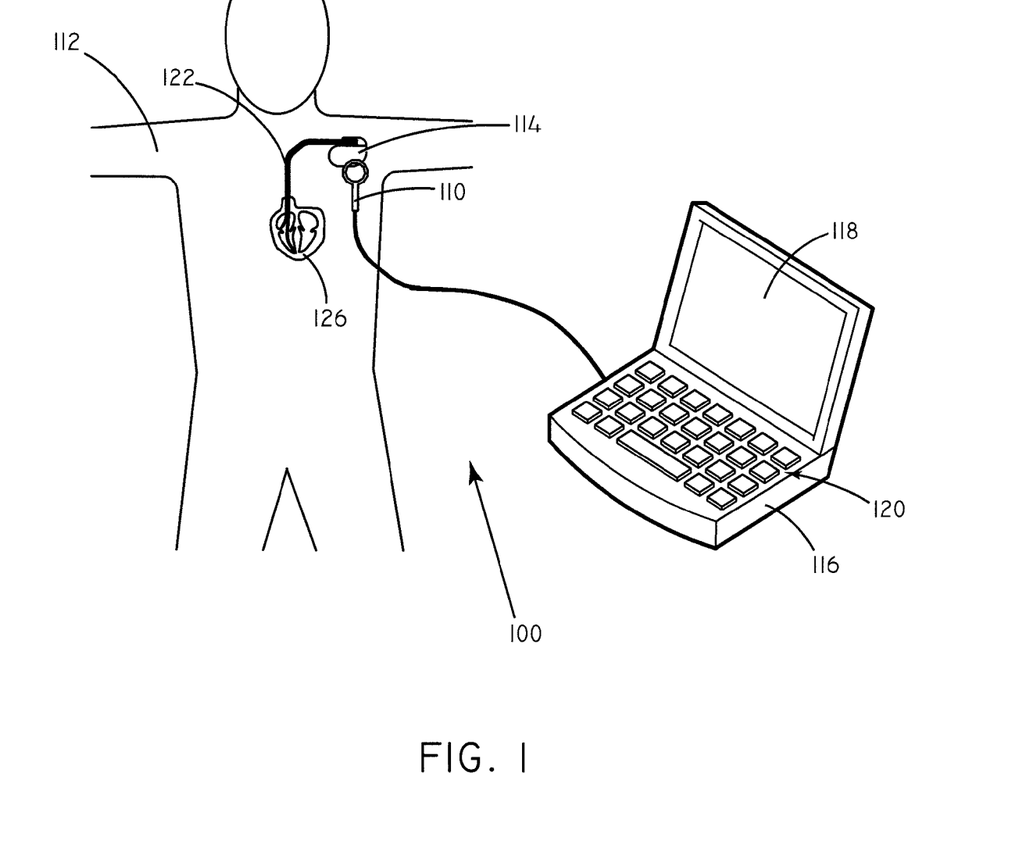
FIG. 1 is a schematic of an exemplary implementation, consistent with at least one embodiment of the invention.

FIG. 1 is a schematic of an exemplary system 100, consistent with at least one embodiment of the invention. The system 100 can include an implantable medical device 114 disposed within a patient 112. The implantable medical device 114 can be of various types such as, for example, a pacemaker, a cardioverter-defibrillator, a cardiac resynchronization device, a neuromodulation device, an implantable monitor, or the like. One example of an implantable medical device is disclosed in commonly assigned U.S. Pat. No. 4,562,841, the content of which is herein incorporated by reference in its entirety. In some embodiments, the implantable medical device 114 can include one or more leads 122 disposed in or near the patient's heart 126.

The implantable medical device 114 can be in communication with an external medical device 116. In some embodiments, communication between the implantable medical device 114 and the external medical device 116 can be via inductive communication through a wand 110 held on the outside of the patient 112 near the implantable medical device 114. However, in other embodiments, communication can be carried out via radiofrequency transmission, acoustically, or the like.

The implantable medical device 114 can include one or more implantable sensors in order to gather data regarding the patient 112. Exemplary implantable sensors and types of data are described in greater detail below.

The implantable medical device 114 can be configured to store data over a period of time, and periodically communicate with the external medical device 116 in order to transmit some or all of the stored data.

The external medical device 116 can include a video output device, such as a display screen 118 for displaying video output. In some embodiments, the external medical device 116 can be configured to process the gathered data. The external medical device 116 can also include a user input device 120, such as a keyboard. The external medical system 116 can be for example, a programmer/recorder/monitor device, a computer, an advanced patient management system, or a personal digital assistant (PDA). Exemplary programmer/recorder/monitor devices include the Model 3120 Programmer, available from Boston Scientific Corporation, Natick, Mass.

The external medical system 116 can display real-time data or stored data graphically, such as in charts or graphs, and textually. Notably, the external medical system 116 can be configured to display information in a first format and a second format simultaneously. The first format can be a graphical format and the second format can be a textual format.

Figure 2:
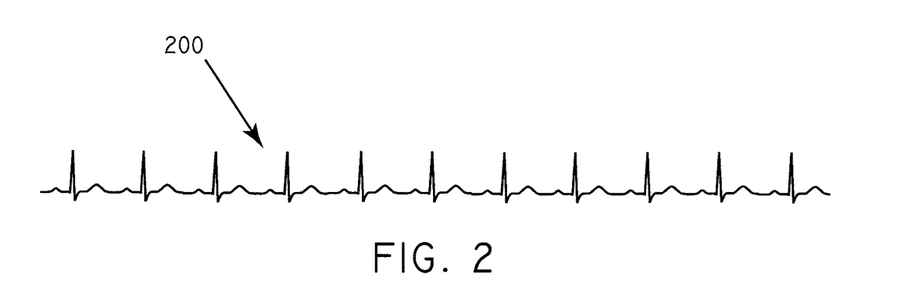
FIG. 2 provides an example of graphical data consistent with multiple embodiments of the invention.

The graphical data displayed by the external medical system 116 can include many different types of data gathered by sensors, such as those types described in greater detail below. As a specific example, FIG. 2 shows electrogram data 200 displayed in a graphical format. The electrogram data 200 reflects the electrical activity associated with cardiac cycles of a hypothetical patient.

Figure 3:
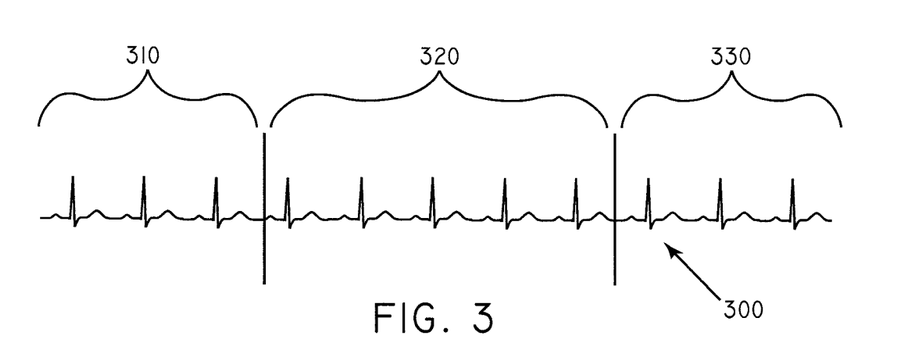
FIG. 3 provides an example of graphical data consistent with multiple embodiments of the invention.

In various embodiments, the data displayed in a graphical format can be divided into a plurality of phases. FIG. 3 represents an example of electrogram data 300 divided into a first phase 310, second phase 320, and third phase 330. It will be appreciated that there are many different ways of dividing a set of data into subsets or phases. In this example, the phases 310, 320, and 330 each can encompass a specific subset of data points that have features in common, such as the specific time period within which the data was gathered. As another example, the phases 310, 320, and 330 can represent different stages in treatment, health, or illness.

In one example, the first phase 310 represents an "onset phase", which can be the onset of an episode of interest, such as the onset of a cardiac arrhythmia. By way of example, the "onset phase" can include data showing the progression of a patient from a normal physiological state to an abnormal physiological state requiring treatment.

The second phase 320 can represent a "therapy phase", which can be the treatment period of an illness or episode, such as the period during which electrical stimulation is administered to a patient's heart. Data from the therapy phase may include data showing the relative timing of the electrical stimulation along with the activity of the patient's heart in response to the stimulation. In some embodiments, the data set can include multiple therapy phases.

The third phase 330 can represent an "end phase", which can be the period of time following treatment of an episode or illness. Data from the end phase can include data showing the patient returning to a normal physiological state and/or can include data that illustrates why the therapy phase was terminated.

It will be appreciated that the data can be divided into any number of phases that is desirable. In some embodiments, data may be divided up into as few as two different phases. In other embodiments, data may be divided up into twenty or more phases. In some embodiments, the division between phases can be automatically determined by the system. In other embodiments, the division between phases can be entered by a system user.

In accordance with embodiments herein, graphical data, such as that displayed in FIGS. 2-3 can have textual data associated with a particular point, phase, or part of the graph. This textual data can be items of particular interest or importance to a clinician or user. Extending the example described with respect to FIG. 3 above, during the onset phase the data of particular interest to a clinician may include the maximum heart rate measured during the phase and/or the change in various hemodynamic parameters before the onset of a condition, such as an arrhythmia. However, data regarding electrical stimulation, such as applied voltage, may be omitted during the onset phase since stimulation is generally not administered during the "onset phase", such as with the onset of a tachyarrhythmia. As such, the data of particular interest is contextual. In various embodiments, the system can be configured to show only data that is of particular interest with respect to a particular phase. Therefore, the overall display of data can be simplified and made more conducive to quick uptake by a clinician or system user.

Figure 4:
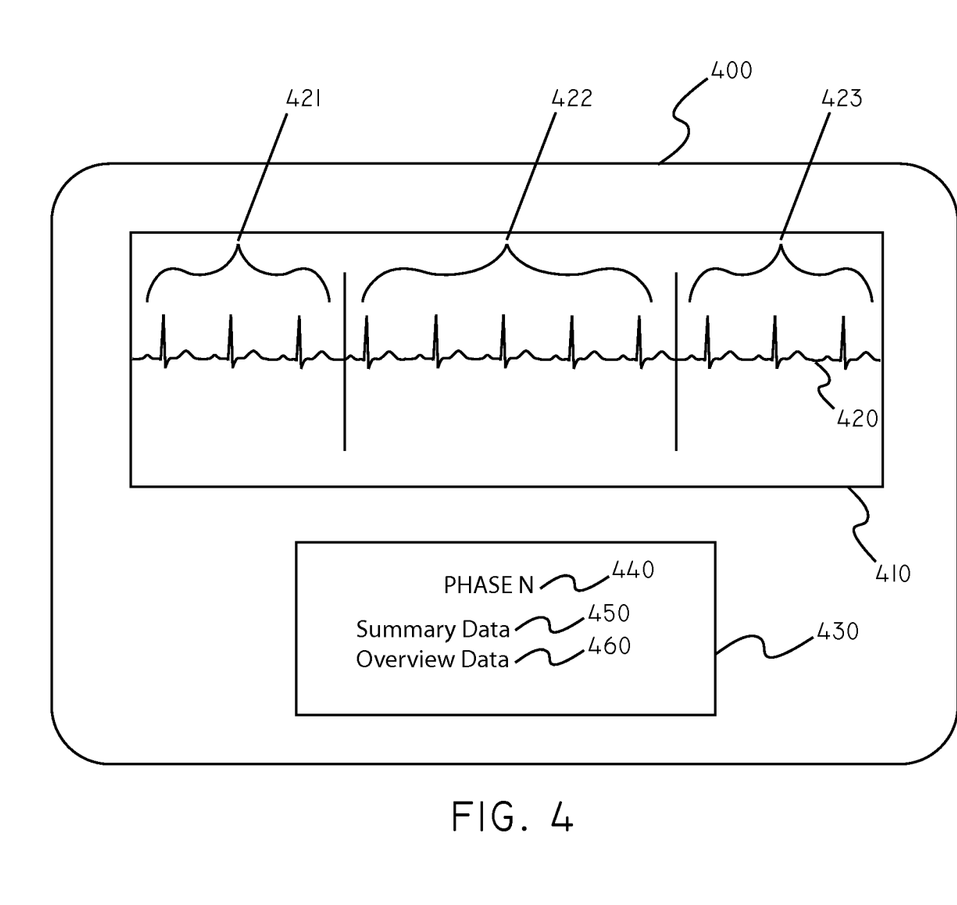
FIG. 4 is a schematic view of an exemplary display screen consistent with multiple embodiments of the invention.

FIG. 4 is a schematic diagram of an exemplary display screen 400 provided through a video output consistent with multiple embodiments of the invention. The display screen 400 defines a first data area 410 configured to display graphical data 420. In this example, the graphical data 420 is divided into a first phase 421, a second phase 422, and a third phase 423. The display screen 400 also defines a second data area 430 configured to display textual data that can include correlated data such as summary data 450 and/or overview data 460 regarding a user-selected phase. In some embodiments, the second data area 430 can also display the identity of the phase that is currently selected 440.

The display screen 400 can be any type of video output device that can display graphical data as well as textual data. The display screen 400 can be a computer monitor, for example. The display screen 400 is attached to a video output controller which in turn is in communication with at least one processing device that organizes and gathers the data to be displayed.

In multiple embodiments, there is a user input interface that gives a user the ability to select a particular phase of graphical data 420, amongst other things. The user input interface can include a user input device such as a keyboard, a trackball, a mouse, a stylus, a touch screen, or the like. In one embodiment, the user input interface is a computer mouse. In some embodiments, if a particular phase is selected by a user, the processor can be configured to display more specific data associated with the selected phase on the display screen 400. For example, as a user manipulates a computer mouse to select a particular phase of the graphical data 420 by depressing a mouse button, the textual data 440, 450, and/or 460 changes to reflect the currently selected phase.

Correlated data such as summary data 450 and/or overview data 460 can provide many items of interest to a clinician. For example, summary data 450 and/or overview data 460 can help interpret the graph, can report trends surrounding the portion of graph that is of interest, report data regarding specific points on the graph, summarize the selected phase or phases, and/or provide any other information of interest relevant to the graphical data or patient health generally. Summary data 450 and/or overview data 460 can include but is not limited to data such as maximum, average, or variance of the R-R interval, beats per minute, P-R interval, impedance, and the like.

Figure 5:
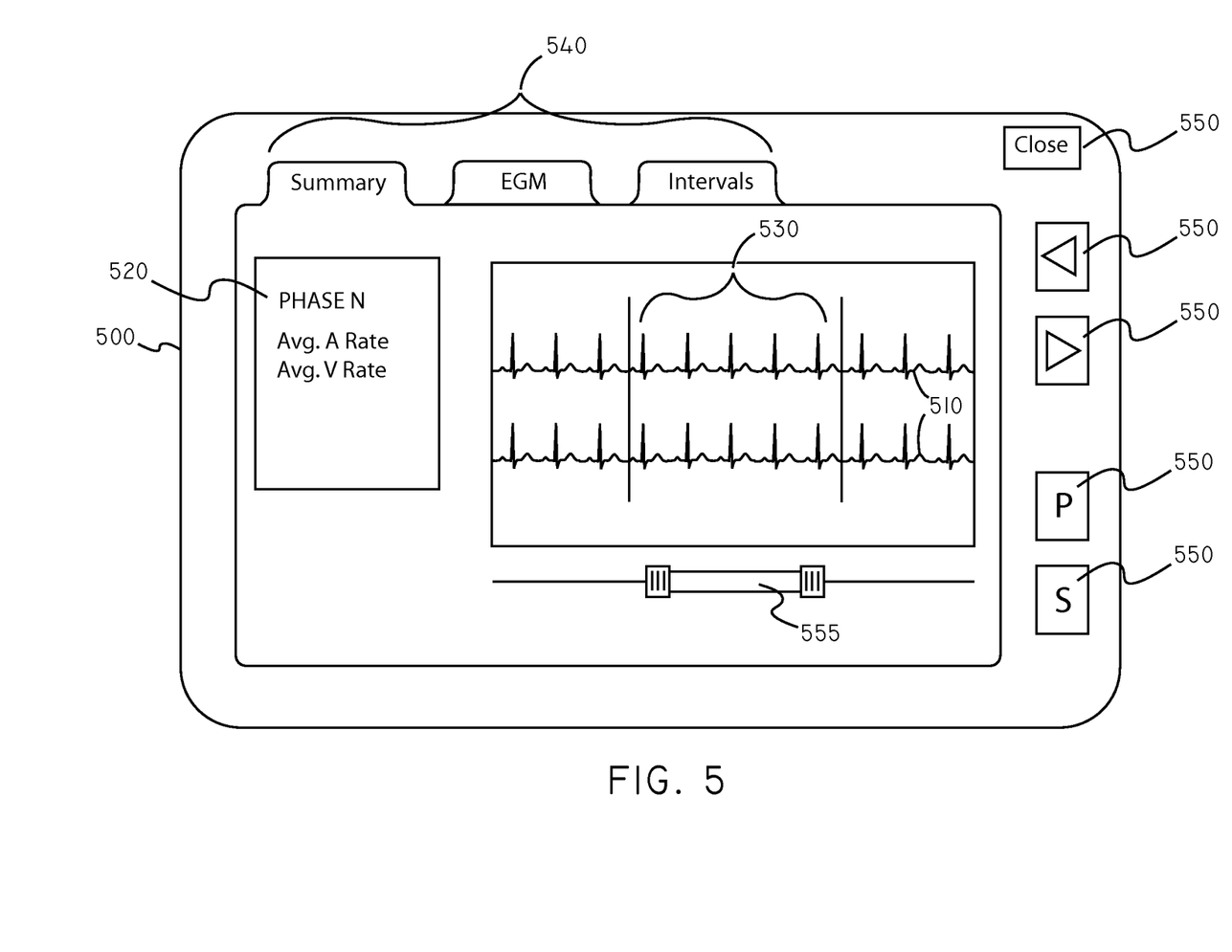
FIG. 5 is a schematic view of an exemplary display screen consistent with multiple embodiments of the invention.

It will be appreciated that the display screen can include a variety of different features in order to facilitate usage by a clinician. FIG. 5 is an exemplary display screen consistent with at least one embodiment of the invention. Textual data 520 and graphical data 510 are disposed on the display screen 500 for one particular phase 530. Tabs 540 disposed along an edge of the display screen 500 provide options for the viewer to access different types of information. Various electronic buttons 550 provide additional options for the viewer to move between groups of data (including, in some embodiments, alternate phases in the same set of data), printing options, and saving options. In some embodiments, a slider bar 555 can be included on the display screen in order to facilitate the selection of a particular phase of graphical data. Other options may also be provided to allow viewers to quickly manipulate and use data.

Figure 6:
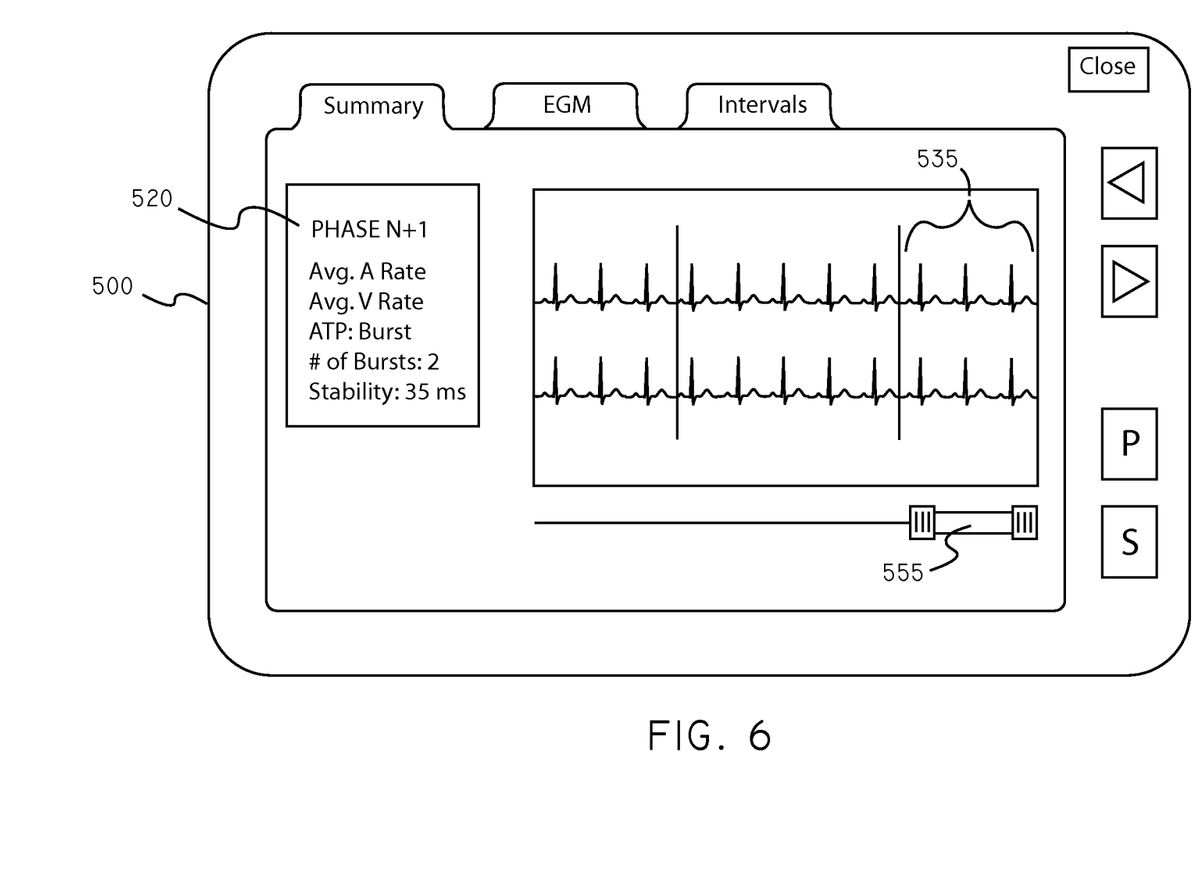
FIG. 6 is a schematic view of an exemplary display screen consistent with multiple embodiments of the invention.

As described above, the textual data that is provided can change depending on the phase of the graphical data that is selected by the user. FIG. 6 is an exemplary display screen consistent with at least one embodiment of the invention, demonstrating changes in display associated with user selection of a different phase. In FIG. 6, a particular phase 535 has been selected by way of moving slider bar 555 that is different from the phase selected in FIG. 5. As such, the corresponding textual data 520 that is displayed includes different elements than that shown in FIG. 5.

Figure 7:
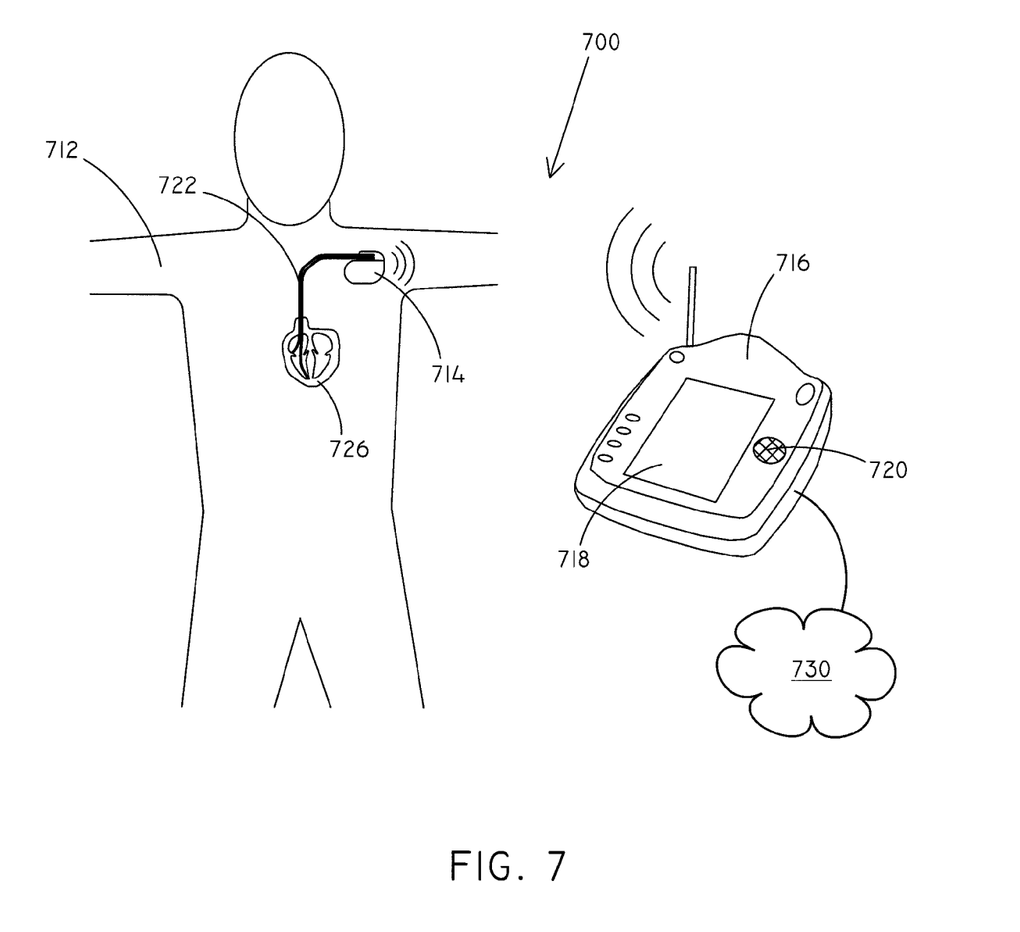
FIG. 7 is a schematic of an exemplary implementation, consistent with at least one embodiment of the invention.

It will be appreciated that the external device or medical system that can be used to display data can take on many different forms. FIG. 7 is a schematic of an implementation, in accordance with various embodiments. An implantable device 714, implanted within a patient 712, is in communication with an external device 716 that can have a video output in the form of a display screen 718 and an audio output in the form of a speaker 720. Communication can be through radio frequency, inductive transmission, acoustically, or any other means available.

The external device 716 can be an in-home monitoring system for use by a patient in their home or residence. An exemplary in-home monitoring system is the LATITUDE® patient management system, available from Boston Scientific Corporation, Natick, Mass. Aspects of exemplary in-home monitoring systems are described in U.S. Pat. No. 6,978,182, the content of which is herein incorporated by reference in its entirety. In such a situation, the external device 716 can be in communication with an additional processing device such as a workstation or server remote from the external device 716 to enable access to the information by doctors or technicians. For example, the external device 716 can be in communication with a workstation or server through the Internet 730 or another type of data connection. In some embodiments, the external device can be a mobile device (not shown), such as a hand-held device or a device worn on a belt.

Figure 8:
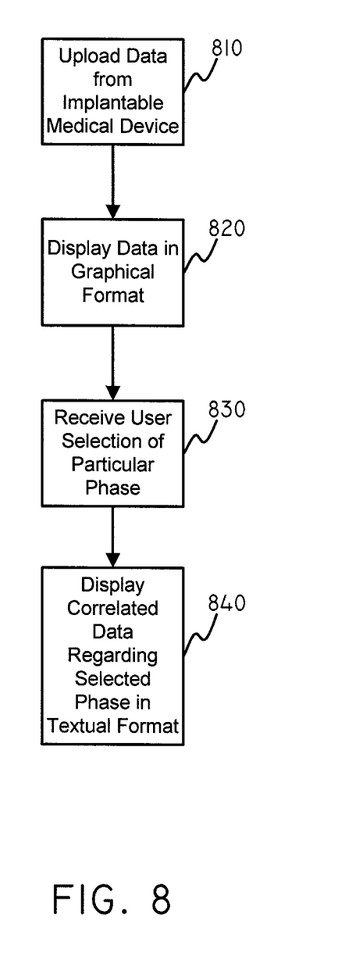
FIG. 8 is a flow diagram in accordance with an embodiment of the invention.

Embodiments of the invention can also include various methods. FIG. 8 is a flow diagram of a method in accordance with at least one embodiment. In one operation, the method includes communicating with an implantable medical device 810. Communicating with an implantable medical device can specifically include uploading data from the implantable medical device. Communication may be via radio frequency, induction, or acoustically, for example. The data provided by the implantable medical device may be stored data or may be real-time data.

In another operation, the method includes providing an image on a graphical display 820. Providing an image on a graphical display 820 can specifically include displaying data in a graphical format. Providing an image on a graphical display 820 can also include dividing the graphical data into multiple phases over time, and providing a visual indication on the graphical data of phase locations.

In another operation, the method includes receiving a user selection of a particular phase 830. Receiving a user selection of a particular phase 830 can occur through a user input interface as discussed above. A user can use a keyboard, computer mouse, or keypad, as examples, to select a particular phase.

In another operation, the method includes displaying information regarding the particular phase in a textual format 840. Displaying information regarding the particular phase 840 will generally be in response to receiving the user selection, although embodiments are contemplated where information regarding a particular phase is provided automatically without having received a user selection.

It will be appreciated that the operations included in this exemplary method are not limited to a particular progression of events unless otherwise noted. Any progression is appropriate that allows the technology discussed herein to be realized.

In some embodiments, the invention includes a device including a graphical display and a machine-readable medium comprising instructions. The instructions can perform various operations when implemented by one or more processors. By way of example, the operations can include those in accordance with methods as described herein. The machine-readable medium can include random access memory (RAM), read-only memory (ROM), magnetic data storage media, optical data storage media, flash memory and the like.

Figure 9:
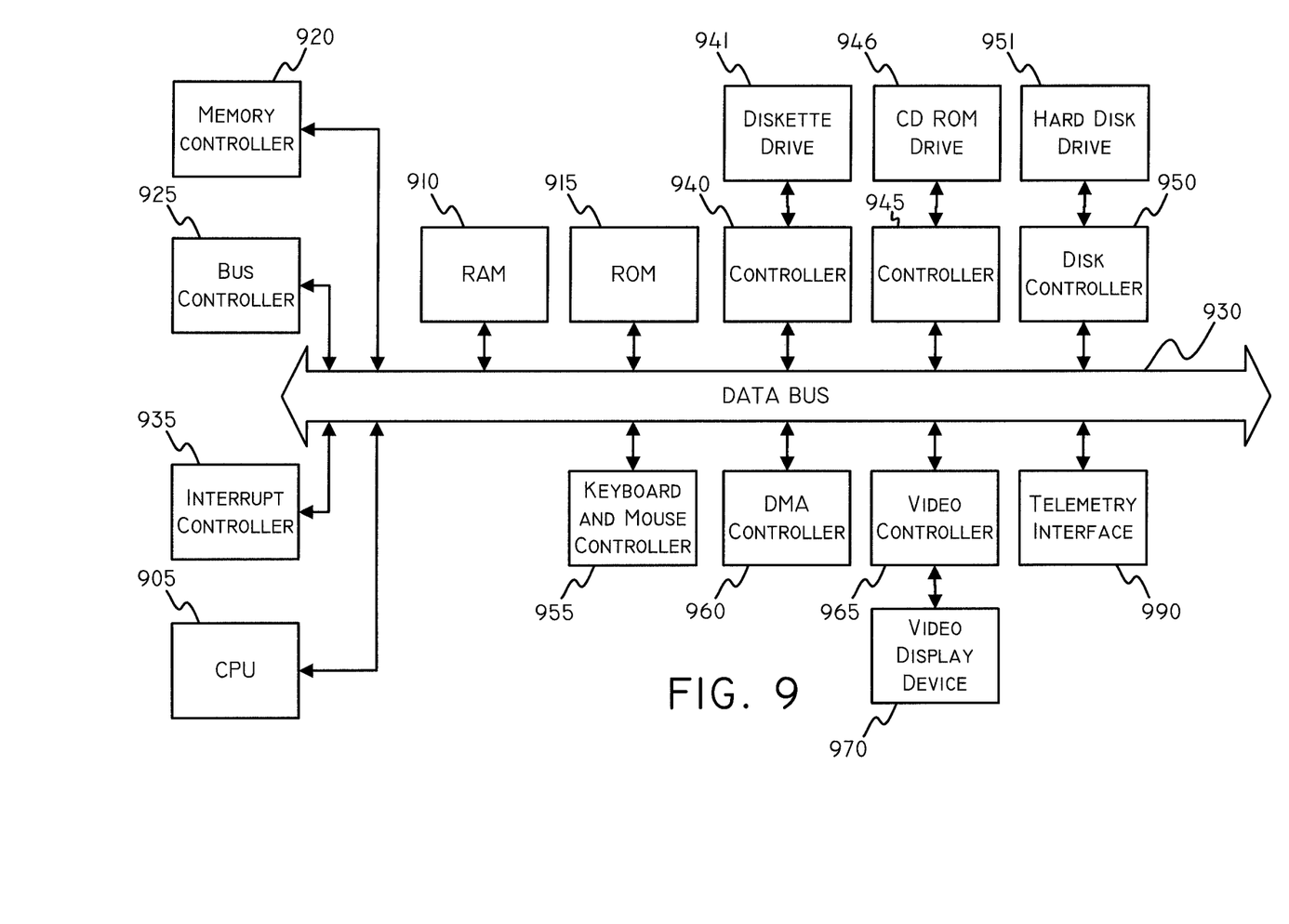
FIG. 9 is a schematic diagram of various programmer/recorder/monitor components in accordance with various embodiments of the invention.

External devices to display information, such as programmer/recorder/monitors, can include components common to many computing devices. Referring now to FIG. 9, a diagram of various components is shown in accordance with some embodiments of the invention. The external system includes a central processing unit (CPU) 905 or processor, which may include a conventional microprocessor, random access memory (RAM) 910 for temporary storage of information, and read only memory (ROM) 915 for permanent storage of information. A memory controller 920 is provided for controlling system RAM 910. A bus controller 925 is provided for controlling data bus 930, and an interrupt controller 935 is used for receiving and processing various interrupt signals from the other system components.

Mass storage can be provided by diskette drive 941, which is connected to bus 930 by controller 940, CD-ROM drive 946, which is connected to bus 930 by controller 945, and hard disk drive 951, which is connected to bus 930 by controller 950. User input to the programmer system may be provided by a number of devices. For example, a keyboard and mouse can connected to bus 930 by keyboard and mouse controller 955. DMA controller 960 is provided for performing direct memory access to system RAM 910. A visual display is generated by a video controller 965 or video output, which controls video display 970. The external system can also include a telemetry interface 990 or telemetry circuit which allows the external system to interface and exchange data with an implantable medical device. It will be appreciated that some embodiments may lack various elements illustrated in FIG. 9.

Types of Sensors and Sensor Data

Various embodiments of systems included here can include an implantable device with one or more implantable sensors. Exemplary implantable sensors can be configured to gather data that may be relevant or of interest to a patient, doctor, technician, or the like, in the diagnosis and/or treatment of a condition. In some embodiments, the sensor can include one or more electrodes in order to gather electrical data regarding the patient. In other embodiments, the sensor can be a pressure sensor. Exemplary pressure sensors are described in U.S. Pat. No. 6,237,398, herein incorporated by reference in its entirety. In still other embodiments, the sensor can be an accelerometer. Exemplary accelerometers are described in U.S. Pat. No. 6,937,900, herein incorporated by reference in its entirety. In some embodiments, the sensor can be a chemical sensor. Exemplary chemical sensors are described in U.S. patent application Ser. No. 11/383,933, herein incorporated by reference in its entirety.

Figure 10:
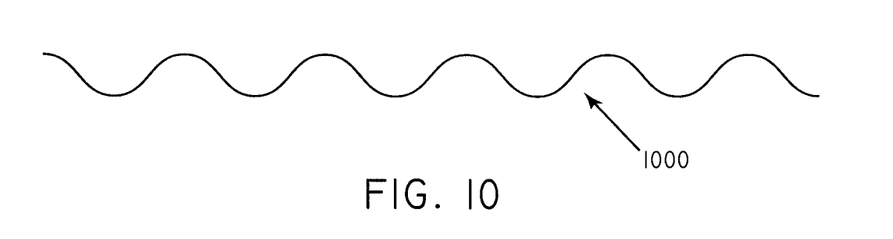
FIG. 10 provides an example of graphical data consistent with multiple embodiments of the invention.

The data that is gathered by the sensor(s) can be of many different types. As displayed in FIGS. 2-3, the data can include electrogram data. However, the data can also include, but is not limited to, heart rate data, pressure data, volume data, flow rate data, temperature data, chemical analyte data, activity data, and accelerometer data. FIG. 10 is a graph of an exemplary data set 1000. The data set shown in FIG. 10 follows a roughly sinusoidal pattern. This data can represent pressure changes or flow rates, amongst other things.

Figure 11:
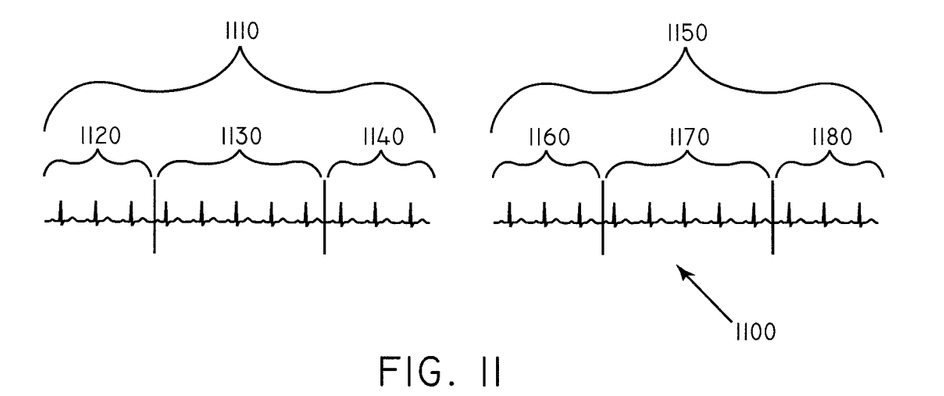
FIG. 11 provides an example of graphical data consistent with multiple embodiments of the invention.

Though graphical data is discussed herein as being divided into a plurality of phases in various embodiments, it will be appreciated that there are many different ways of organizing sets of data. By way of example, in some embodiments, multiple tiered groupings of data can be made. Referring now to FIG. 11, graphical data 1100 is shown grouped at two separate levels. Specifically, the graphical data 1100 is grouped into a first episode 1110 and a second episode 1150. The data of the first episode 1110 is then further broken down into a first phase 1120, a second phase 1130, and a third phase 1140. Similarly, the data of the second episode 1150 is further broken down into a first phase 1160, a second phase 1170, and a third phase 1180. The user of a system can make a selection on one or both tiers of data organization. By way of example, the user of a system can select either the first or second episode and/or select a particular phase within either the first or second episode. Once a selection is made, textual data can be displayed corresponding to the particular episode and/or phase that has been selected. When a different episode and/or phase is selected, the textual data can change to reflect the newly selected episode and/or phase.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A medical system comprising:
   a video output; and
   a processor in communication with video output, the system configured to display electrogram information regarding a patient in a first format and a second format through the video output simultaneously, the first format comprising primary data in a graphical format and the second format comprising secondary data in a textual format, the primary data divided into a plurality of phases relevant to treatment comprising an onset phase, a therapy phase, and an end phase, the secondary data comprising at least one of an average, maximum, or variance of data from one of the plurality of phases, wherein the system is configured to automatically change the type of information displayed in the second format based on user selection of one of the plurality of phases; wherein when an onset phase is selected the information displayed in the second format includes the average atrial rate and the average ventricular rate and when a therapy phase is selected the information displayed in the second format includes ATP information; wherein the information displayed comprises data generated from an implanted sensor.

2. The medical system of claim 1, wherein the system is configured to automatically divide the primary data into a plurality of phases.

3. The medical system of claim 1, wherein the second format comprises a tabular display.

4. The medical system of claim 1 further comprising a slider bar configured to facilitate the selection of a particular phase of graphical data.

5. The medical system of claim 1, further comprising a telemetry circuit configured to receive information regarding the patient from an implanted medical device.

6. The medical system of claim 1, the medical system comprising an in-home monitoring system.

7. The medical system of claim 1, the medical system comprising a programmer/recorder/monitor (PRM) device.

8. A medical system comprising:
   an implanted medical device; and
   an external medical system comprising
      a telemetry circuit configured to receive information regarding a patient from the implanted medical device;
      a video output; and
      a processor,
   the system configured to display data regarding the patient divided into a plurality of phases relevant to treatment comprising an onset phase, a therapy phase, and an end phase and simultaneously display overview data regarding a particular user-selected phase, the system configured to automatically change the type of overview data as the particular user-selected phase changes, wherein the overview data comprises at least one of average, maximum, or variance data; wherein when an onset phase is selected the overview data includes the average atrial rate and the average ventricular rate and when a therapy phase is selected the overview data includes ATP information; wherein the data displayed comprises data generated from an implanted sensor.

9. The medical system of claim 8, the external medical system comprising an in-home monitoring system.

10. The medical system of claim 8, the external medical system comprising a programmer/recorder/monitor (PRM) device.

* * * * *